(12) United States Patent
Li et al.

(10) Patent No.: US 7,158,219 B2
(45) Date of Patent: Jan. 2, 2007

(54) SERS-ACTIVE STRUCTURES INCLUDING NANOWIRES

(75) Inventors: Zhiyong Li, Palo Alto, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/942,693

(22) Filed: Sep. 16, 2004

(65) Prior Publication Data
US 2006/0054881 A1 Mar. 16, 2006

(51) Int. Cl.
*G01N 1/00* (2006.01)
*G01J 3/44* (2006.01)

(52) U.S. Cl. ........................... 356/36; 356/301
(58) Field of Classification Search ............... 356/36, 356/301
See application file for complete search history.

(56) References Cited

U.S. PATENT DOCUMENTS

| | | |
|---|---|---|
| 4,674,878 A | 6/1987 | Vo-Dinh |
| 4,944,985 A | 7/1990 | Alexander et al. |
| 5,017,007 A | 5/1991 | Milne et al. |
| 5,255,067 A | 10/1993 | Carrabba et al. |
| 5,527,712 A | 6/1996 | Sheehy |
| 5,609,907 A | 3/1997 | Natan |
| 5,772,905 A | 6/1998 | Chou |
| 5,837,552 A | 11/1998 | Cotton et al. |
| 6,149,868 A | 11/2000 | Natan et al. |
| 6,165,911 A | 12/2000 | Calveley |
| 6,361,861 B1 * | 3/2002 | Gao et al. .................... 428/367 |
| 6,365,059 B1 | 4/2002 | Pechenik |
| 6,406,777 B1 | 6/2002 | Boss et al. |
| 6,432,740 B1 | 8/2002 | Chen |
| 6,623,977 B1 | 9/2003 | Farquharson et al. |
| 6,649,683 B1 | 11/2003 | Bell |
| 6,743,368 B1 | 6/2004 | Lee |
| 6,773,616 B1 | 8/2004 | Chen et al. |
| 7,011,771 B1 * | 3/2006 | Gao et al. .................... 252/502 |
| 2002/0123050 A1 * | 9/2002 | Poponin ........................ 435/6 |
| 2002/0142480 A1 | 10/2002 | Natan |
| 2003/0120137 A1 | 6/2003 | Paw luczyk |
| 2003/0143453 A1 * | 7/2003 | Ren et al. ..................... 429/40 |
| 2003/0165418 A1 * | 9/2003 | Ajayan et al. ........... 423/447.2 |
| 2003/0231304 A1 | 12/2003 | Chan et al. |
| 2004/0135997 A1 | 7/2004 | Chan et al. |
| 2004/0175844 A1 * | 9/2004 | Yang et al. ..................... 438/2 |
| 2006/0038990 A1 * | 2/2006 | Habib et al. ................. 356/301 |

OTHER PUBLICATIONS

Drew, Christopher, et al., "Metal Oxide-Coated Polymer Nanofibers," Nano Letters, vol. 3, No. 2, 2003, pp. 143-147.
Emory, Steven R., et al., "Screening and Enrichment of Metal Nanoparticles with Novel Optical Properties," J. Phys. Chem. B, vol. 102, No. 3, 1998, pp. 493-496.
Green, Mino, et al., "SERS Substrates Fabricated by Island Lithography: The Silver/Pyridine System," J. Phys. Chem. B, vol. 107, No. 47, 2003, pp. 13015-13021.

(Continued)

*Primary Examiner*—Evan Pert

(57) ABSTRACT

A SERS-active structure is disclosed that includes a substrate and at least one nanowire disposed on the substrate. The at least one nanowire includes a core including a first material and a coating including a SERS-active material. A SERS system is also disclosed that includes a SERS-active structure. Also disclosed are methods for forming a SERS-active structure and methods for performing SERS with SERS-active structures.

15 Claims, 8 Drawing Sheets

OTHER PUBLICATIONS

Kamins, T.J., et al., "Chemically vapor deposited Si nanowires nucleated by self-assembled Ti islands on patterned and unpatterned Si substrates," Physica E 13, 2002, pp. 995-998.

Kneipp, Katrin, et al., "Single Molecule Detection Using Surface-Enhanced Raman Scattering (SERS)," Physical Review Letters, vol. 78, No. 9, Mar. 3, 1997, pp. 1667-1670.

Liu, Fong-Ming, et al., "Efficient SERS substrates made by electroless silver deposition into patterned silicon structures," J. Mater. Chem., 14, 2004, pp. 1526-1532.

Michaels, Amy M., et al., "Surface Enhanced Raman Spectroscopy of Individual Rhodamine 6G Molecules on Large Ag Nanocrystals," J. Am. Chem. Soc., vol. 121, No. 43, 1999, pp. 9932-9939.

Pinto, N.J., et al., "Electroless Deposition of Thin Metallic Films on Polymer Fibers Prepared via Electrospinning," Polymer Preprints, 44(2), 138, 2003, pp. 138-139.

Tao, Andrea, et al., "Langmuir-Blodgett Silver Nanowire Monolayers for Molecular Sensing Using Surface-Enhanced Raman Spectroscopy," Nano Letters, vol. 3, No. 9, 2003, pp. 1229-1233.

* cited by examiner

SERS-ACTIVE STRUCTURES INCLUDING NANOWIRES

FIELD OF THE INVENTION

The invention relates to surface enhanced Raman spectroscopy (SERS). More particularly, the invention relates to SERS-active structures including features having nanoscale dimensions, methods for forming SERS-active structures, and methods for performing SERS using SERS-active structures.

BACKGROUND OF THE INVENTION

Raman spectroscopy is a well-known technique for performing chemical analysis. In conventional Raman spectroscopy, high intensity monochromatic light provided by a light source, such as a laser, is directed onto an analyte (or sample) that is to be chemically analyzed. A majority of the incident photons are elastically scattered by the analyte molecule. In other words, the scattered photons have the same energy, and thus the same frequency, as the photons that were incident on the analyte. However, a small fraction of the photons (i.e., about 1 in $10^7$ photons) are inelastically scattered by the analyte molecules. These inelastically scattered photons have a different frequency than the incident photons. This inelastic scattering of photons is termed the "Raman effect." The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the "Stokes radiation." A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the "anti-Stokes radiation."

The Stokes and the anti-Stokes radiation is detected by a detector, such as a photomultiplier or a wavelength-dispersive spectrometer, which coverts the energy of the impinging photons into an electrical signal. The characteristics of the electrical signal are at least partially a function of the energy (or wavelength, frequency, wave number, etc.) of the impinging photons and the number of the impinging photons (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the frequency of the inelastically scattered Raman photons against the intensity thereof. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to conventional Raman spectroscopy. In SERS, the analyte molecules are adsorbed onto, or placed adjacent to, an activated metal surface or structure (a "SERS-active structure"). The interactions between the molecules and the surface cause an increase in the strength of the Raman signal. The mechanism of Raman signal enhancement exhibited in SERS is not completely understood. Two main theories of enhancement mechanisms have been presented in the literature: electromagnetic enhancement and chemical (or "first layer") enhancement. (For further discussion of these surface enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932–39 (1999)).

Several SERS-active structures have been employed in SERS techniques, including activated electrodes in electrolytic cells, activated metal colloid solutions, and activated metal substrates such as a roughened metal surface or metal "islands" formed on a substrate. For example, it has been shown that adsorbing analyte molecules onto or near a specially roughened metal surface made from gold or silver may enhance the Raman scattering intensity by factors of between $10^3$ and $10^6$.

Recently, SERS has been performed employing randomly oriented nanometer scale needles, particles, and wires, as opposed to a simple roughened metallic surface. The intensity of the Raman scattered photons from a molecule adsorbed on such a metal surface may be increased by factors as high as $10^{14}$. However, the intensity of the Raman scattered photons could be further increased if there was a method for forming SERS-active structures including nanoscale features having well controlled size, shape, location, and orientation. Also, the inability to produce such SERS-active structures is impeding research directed to completely understanding the enhancement mechanisms, and therefore, the ability to optimize the enhancement effect. In addition, SERS-active structures require significant time and money to fabricate. If these problems can be overcome, the performance of nanoscale electronics, optoelectronics, and molecular sensors may be significantly improved.

Accordingly, there is a need for SERS-active structures including nanoscale features having well controlled size, shape, location, and orientation, and a method for their manufacture. In addition, there is a need for a method for producing high quantities of such SERS-active structures at relatively low cost.

BRIEF SUMMARY OF THE INVENTION

The present invention, in a number of embodiments, includes SERS-active structures including features having nanoscale dimensions, methods for forming SERS-active structures, and methods for performing SERS using SERS-active structures.

A SERS-active structure is disclosed that includes a substrate and at least one nanowire disposed on the substrate. The at least one nanowire includes a core including a first material and a coating including a SERS-active material.

A SERS system is disclosed that includes a SERS-active structure, a light source configured to irradiate light onto the SERS-active structure, and a detector configured to receive Raman-scattered light scattered by an analyte when the analyte is located adjacent the SERS-active structure. The SERS-active structure includes a substrate and at least one nanowire disposed on the substrate. The at least one nanowire includes a core having a first material and a coating including a SERS-active material.

A method for performing SERS is disclosed that includes the steps of providing a SERS-active structure, providing an analyte adjacent the SERS-active structure, irradiating the analyte and the SERS-active structure with excitation radiation, and detecting Raman scattered radiation scattered by the analyte. The SERS-active structure includes a substrate and at least one nanowire disposed on the substrate. The at least one nanowire includes a core including a first material and a coating including a SERS-active material.

Also disclosed is a method for forming a SERS-active structure. The method includes the steps of providing a substrate, forming a fractional monolayer of catalyst material on a surface of the substrate, annealing the fractional monolayer of catalyst material to promote self-assembly of at least one nanoisland of catalyst material, exposing the at least one nanoisland of catalyst material to a gas comprising a semiconductor material to promote the formation of at least one nanowire core of semiconductor material, and forming a coating of SERS-active material on the at least one nanowire core.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention, in a number of embodiments, includes SERS-active structures including features having nanoscale dimensions disposed at predetermined locations on a substrate, methods for forming SERS-active structures, SERS systems including SERS-active structures, and methods for performing SERS using such systems.

The methods disclosed herein allow for the fabrication of SERS-active structures, including nanoscale features having well controlled size, shape, and location, which allows for improved enhancement of the Raman scattered signal intensity relative to previous SERS-active structures.

It should be understood that the illustrations presented herein are not meant to be actual views of any particular SERS-active structure, but are merely idealized representations which are employed to describe the present invention. Additionally, elements common between FIGS. 1 through 6 retain the same numerical designation.

Figure 1:
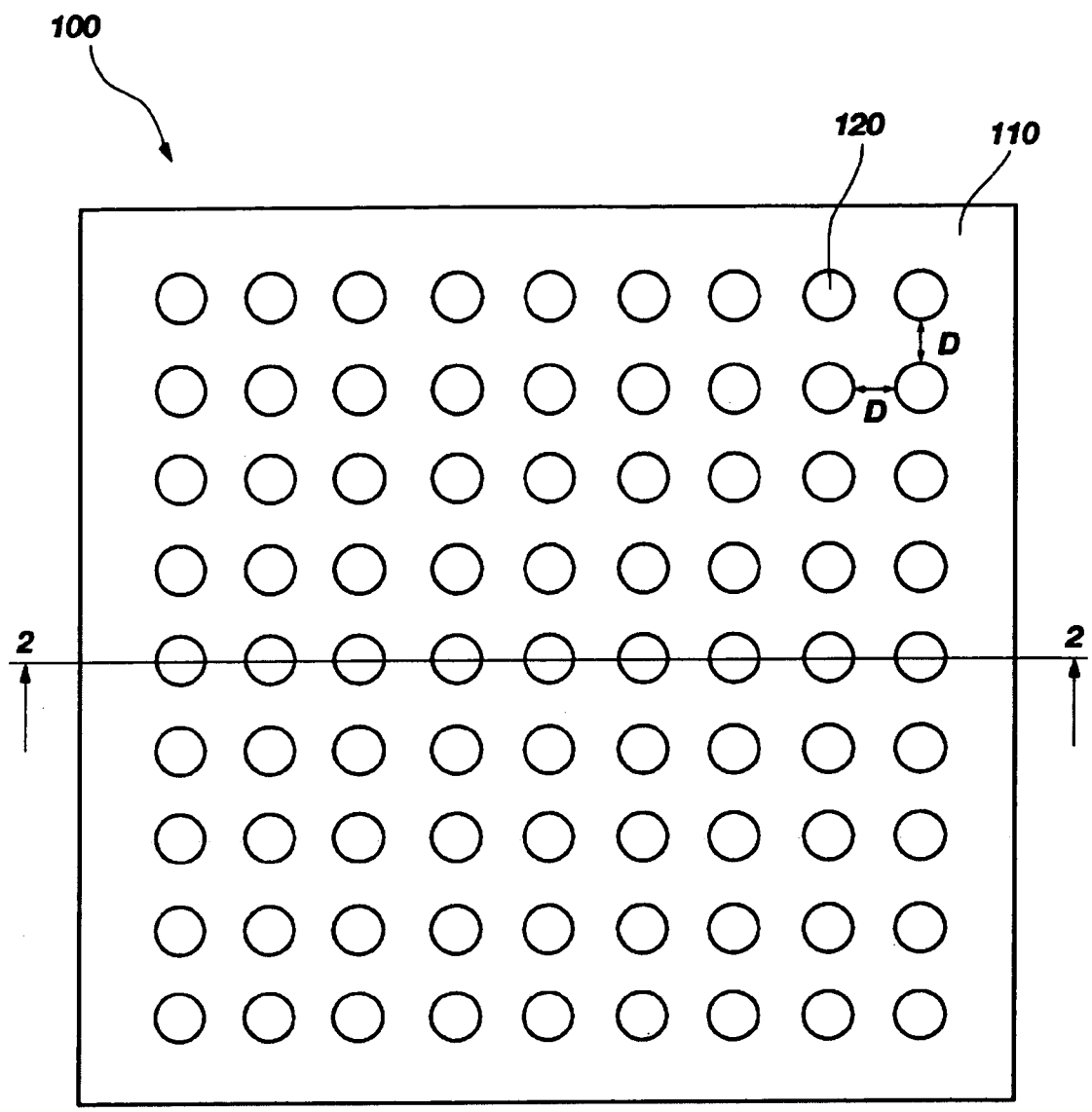
FIG. 1 is a top view of an exemplary embodiment of a SERS-active structure according to the invention.
Figure 2:
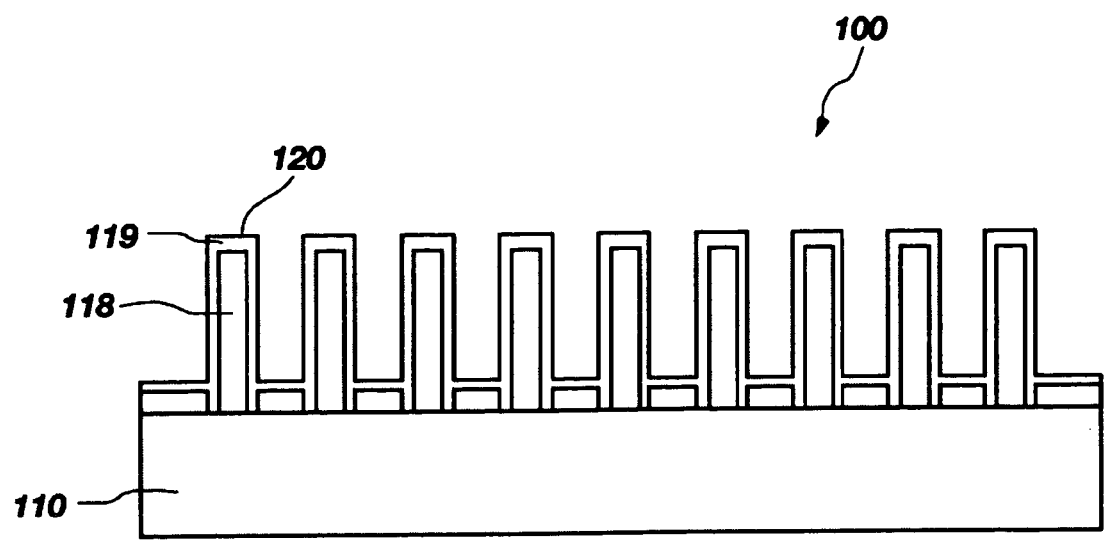
FIG. 2 is a cross-sectional view of the SERS-active structure of FIG. 1 taken along lines 2—2.

An exemplary embodiment of a SERS-active structure according to the invention in shown in FIGS. 1 and 2. A SERS-active structure 100 includes a substrate 110 and at least one nanowire 120 disposed on the substrate 110. The at least one nanowire 120 may extend from a surface of the substrate 110 in a direction substantially perpendicular thereto. As seen in FIG. 2, the at least one nanowire 120 includes a core 118 formed from a first material and a coating 119 including a SERS-active material.

The at least one nanowire 120 may be substantially cylindrical and have a diameter between about 5 and about 50 nanometers. The core 118 of the nanowire 120 also may be substantially cylindrical having a diameter of between about 1 and about 50 nanometers. The coating 119 of the nanowire 120 may have a thickness of between about 0.1 and about 50 nanometers.

The substrate 110 of the SERS-active structure 100 may be formed from, for example, silicon or germanium, or from III–V or II–VI semiconductor materials. The core 118 of the at least one nanowire 120 may be formed from, for example, silicon or germanium, and may include a single crystal. The coating 119 of the at least one nanowire 120 may include any SERS-active material such as, for example, gold, silver, copper, platinum, palladium, aluminum, or any other material that will enhance the Raman scattering of photons by analyte molecules positioned adjacent thereto.

Referring to FIG. 1, the SERS-active structure 110 may include a plurality of nanowires 120 disposed in an array on a surface of the substrate 110, each nanowire 120 of the array being disposed at a predetermined location on the surface of the substrate 110. The exemplary SERS-active structure 110 includes 81 nanowires formed in rows and columns, each nanowire separated from adjacent nanowires by a predetermined distance D (FIG. 1). The predetermined distance D may be between about 1 and about 50 nanometers, but is prefereably between about 1 and about 10 nanometers. In addition, the predetermined distance D may be selected to correspond to the size of a particular analyte molecule to be analyzed with the SERS-active structure 100, such that the molecule is capable of draping between two adjacent nanowires 120, part of the molecule being adsorbed on a first nanowire 120 and another part of the molecule being adsorbed on a second, adjacent nanowire 120. Such a configuration has been shown to significantly enhance the Raman signal emitted by the analyte molecule.

Figure 3:
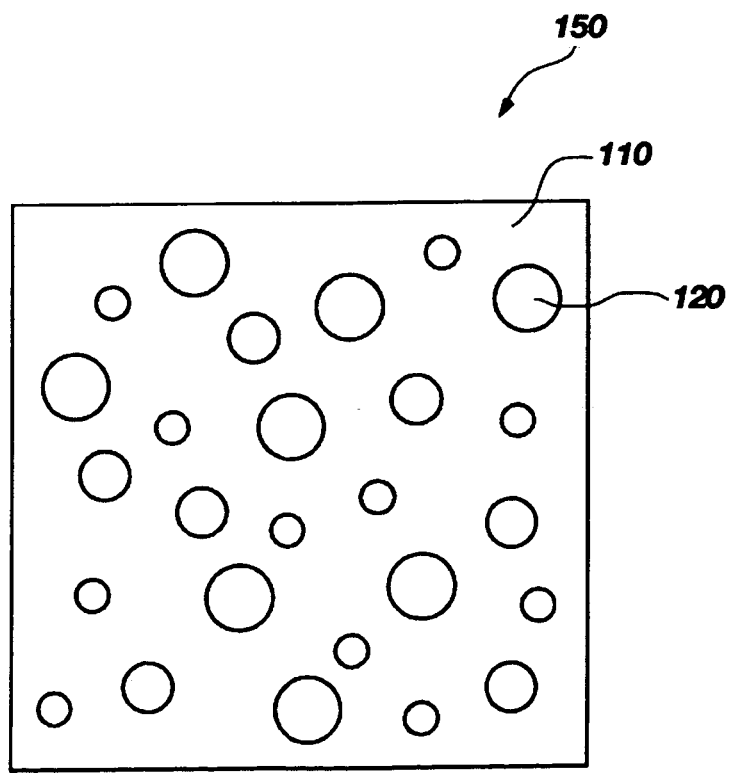
FIG. 3 is a top view of an exemplary embodiment of a SERS-active structure according to the invention.

Another exemplary embodiment of a SERS-active structure according to the invention is shown in FIG. 3. A SERS-active structure 150 includes a substrate 110 and a plurality of nanowires 120 disposed on a surface of the substrate 110. Each nanowire 120 of the plurality of nanowires may extend from a surface of the substrate 110 in a direction substantially perpendicular thereto.

As seen in FIG. 3, each nanowire 120 may have a diameter different from the diameter of other nanowires 120, thereby providing nanowires 120 of varying sizes. In addition, the nanowires 120 are not arranged in rows and columns, or in an array, as are the nanowires 120 of the SERS-active structure 100 (FIG. 1). The nanowires 120 may be separated from adjacent nanowires by a distance that is within a predetermined range, some of the nanowires being spaced closer than others. The predetermined range may be between about 1 and about 50 nanometers, but is prefereably between about 1 and about 10 nanometers. In addition, the predetermined range may be selected to provide a range of distances that correspond to the size of various analyte molecules to be analyzed with the SERS-active structure 150, such that the molecules are capable of spanning between at least two adjacent nanowires 120.

Figure 4A:
FIGS. 4A–4G illustrate an exemplary method for forming the SERS-active structures of FIGS. 1–3.
Figure 4B:
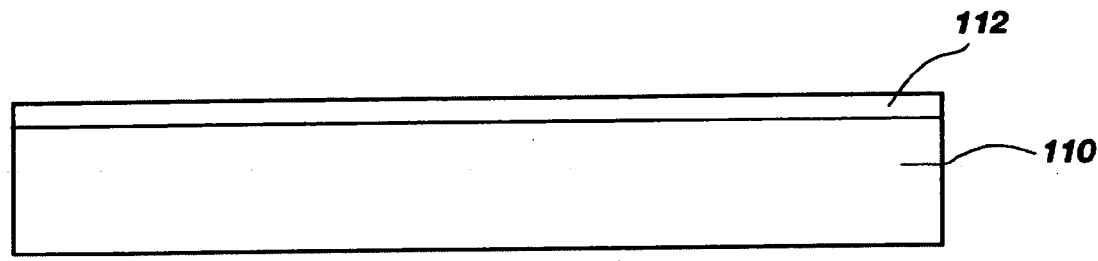

An exemplary method for making the SERS-active structure 100 and the SERS-active structure 150 is illustrated in FIGS. 4A–4F. To produce the SERS-active structure 100, a substrate 110 may be provided as shown in FIG. 4A. The substrate 110 may include a wafer or die of, for example, silicon or germanium, or any other semiconductor material. Next, an oxide layer 112 is formed on or in a surface of the substrate 110 as shown in FIG. 4B. Various methods for forming an oxide layer on or in a surface of a substrate are known in the art of microdevice fabrication.

Figure 4C:
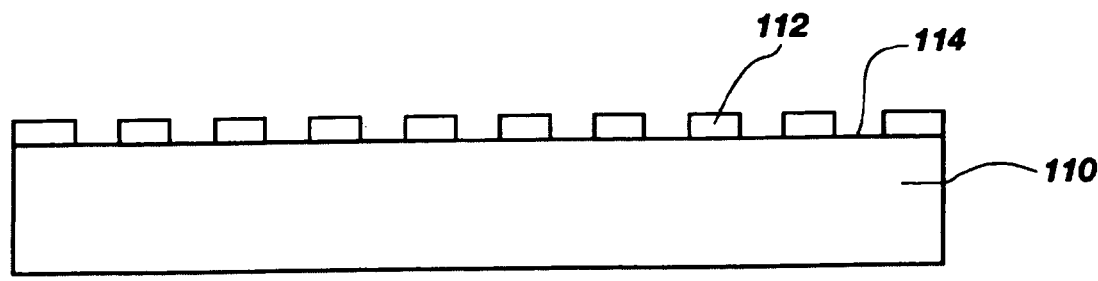

A portion or portions of the oxide layer 112 may be photolithographically removed to form regions of exposed silicon material 114 of the underlying substrate 110, as shown in FIG. 4C. For example, the oxide layer may be masked and etched to remove portions thereof. Each region of exposed silicon material 114 may be disposed at the predetermined locations where the nanowires 120 are to be formed. The regions of exposed silicon material 114 may have substantially the same predetermined size and shape as the core 118 of the nanowires 120.

Figure 4D:
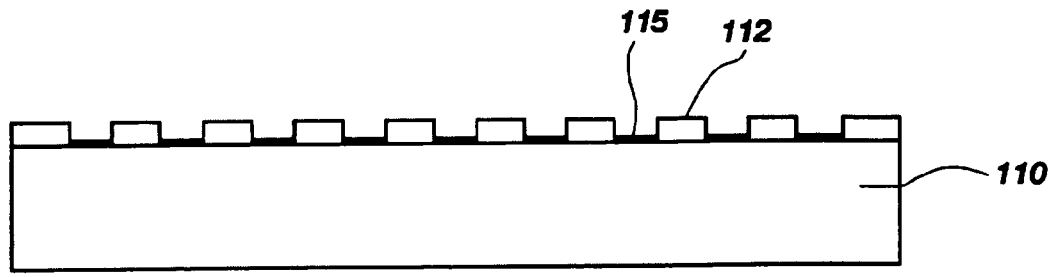

A fractional monolayer of catalyst material 115 is formed or deposited on a surface of the device over the oxide layer 112 and exposed regions of silicon material 114, as shown in FIG. 4D. If the substrate 110 includes silicon, the catalyst material may include titanium. For example, a fractional monolayer 115 of $TiSi_x$ may be deposited preferentially at the exposed regions of silicon material 114, through chemical vapor deposition of Ti, as shown in FIG. 4D. The chemical vapor deposition of titanium may include the decomposition of $TiCl_4$ at temperatures between about 600° C. and about 700° C.

Figure 4E:
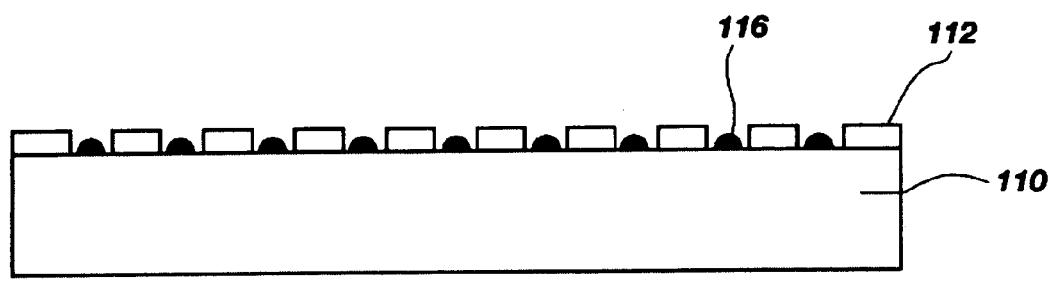

One or more nanoislands 116 of catalyst material may be formed at each region of exposed silicon material 114, as shown in FIG. 4E, by annealing the device at temperatures between about 800° C. and about 1200° C. The size, shape, and number of the nanoislands 116 may be modified by varying the temperature and duration of the annealing process. For example, a large number of small nanoislands may be present after deposition. Many of the small nanoislands may coalesce into a smaller number of larger nanoislands upon annealing.

Figure 4F:

After the nanoislands 116 of catalyst material have been formed at the predetermined locations on the exposed regions of silicon material 114, silicon nanowires may be grown by exposing the device to gases including $SiH_4$ or $SiH_2Cl_2$ at temperatures between about 600° C. and about 700° C. The catalyst material may cause the silicon-containing compounds to decompose and nanowire cores of silicon material may be grown in one dimension, forming the core 118 of the nanowires 120, as shown in FIG. 4F. The length of the growing nanowire cores 118 may correspond to the time duration of the reaction process.

Figure 4G:
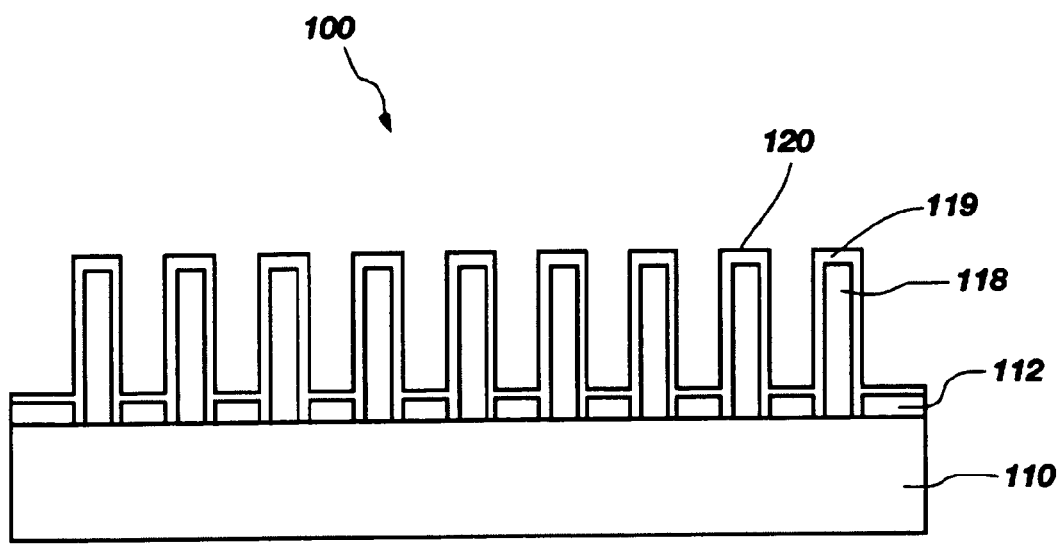

After the cores 118 of the nanowires have been formed, a coating 119 of SERS-active material is deposited over the cores 118 to form the SERS-active structure 100, as shown in FIG. 4G. The SERS-active material may also be deposited over the active surface of the substrate 110, the surface from which the nanowires 120 extend, including any remaining portions of the oxide layer 112. The SERS-active material may include materials such as, for example, gold, silver, copper, platinum, palladium, aluminum, or any other material that will enhance the Raman scattering of photons by analyte molecules positioned adjacent thereto. The coating 119 of SERS-active material may be formed by physical deposition techniques, including but not limited to sputtering, thermal evaporation, and electron beam evaporation. Alternatively, the coating 119 of SERS-active material may be deposited by chemical deposition techniques such as, for example, electroless plating. The thickness of the coating 119 of SERS-active material may be between about 0.1 and about 50 nanometers.

While the nanowires 120 are illustrated in FIGS. 2 and 4G as being of equal length and extending in parallel directions, the nanowires 120 may have varying lengths and may extend in nonparallel directions relative to other nanowires 120.

Alternatively, cores 118 of the nanowires 120 may be formed from germanium. A fractional monolayer of gold may be used as the catalyst material, and germanium nanowires may be grown by exposing the device to gases including $GeH_4$. Many other catalyst materials may also be used including, but not limited to, zinc, platinum, and palladium. Other materials from which the cores 118 may be formed include, but are not limited to, zinc oxide, gallium arsenide, indium phosphide, and carbon materials including diamond.

The method for forming the SERS-active structure 150 is substantially similar to the method for forming the SERS-active structure 100. However, the steps of forming an oxide layer 112 in or on the substrate 110 and forming exposed regions of silicon material 114 at predetermined regions in the oxide layer 112 are omitted and the fractional monolayer of catalyst material 115 and the nanoislands 116 of catalyst material are formed directly on a surface of the substrate 110.

Figure 5A:
FIGS. 5A–5G illustrate an exemplary method for forming the SERS-active structures of FIGS. 1–3.
Figure 5B:
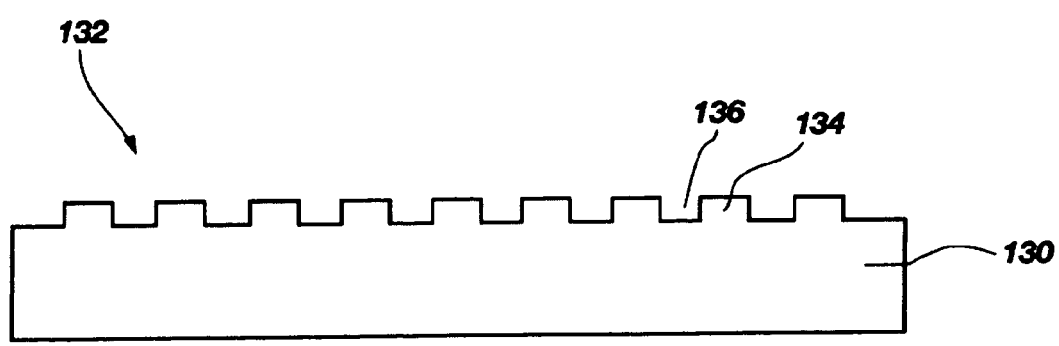
Figure 5C:

An alternative imprinting method for forming the SERS-active structure 100 is illustrated in FIGS. 5A–5G. Referring to FIGS. 5A and 5B, a mold 132 may be formed from a mold substrate 130. The mold substrate 130 may be made from, for example, silicon, other semiconductor materials, ceramics, plastics, metals, or any other suitable material. The mold substrate 130 also may be made from superlattice materials, such as, for example, structures including alternating layers of GaAs and AlAs. A plurality of protrusions 134 and recesses 136 (FIG. 5B) may be formed in a surface of the mold substrate 130 to form the mold 132 using electron beam lithography, reactive ion etching or any other appropriate method known in the art. The size, shape, and location of the protrusions 134 may be substantially identical to the predetermined cross-sectional size, shape, and location of the nanowires 120 to be formed (FIG. 1).

Figure 5D:
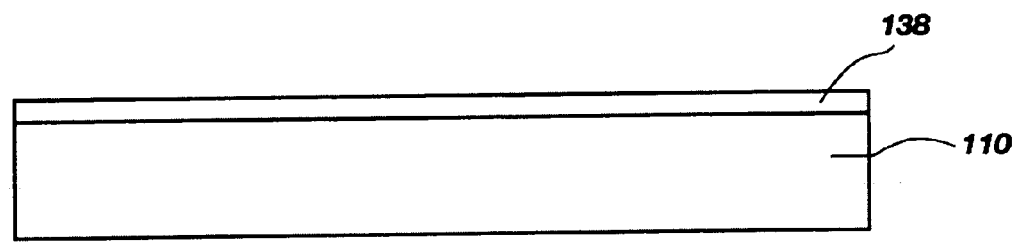

A SERS-active structure substrate 110 may be provided (FIG. 5C), and a layer 138 of deformable material may be applied to a surface thereof (FIG. 5D). The layer 138 of deformable material may include a thermoplastic polymer such as, for example, poly(methyl methacrylate) (PMMA). The thickness of the layer 138 of deformable material may be between about 1 and about 200 nanometers.

Figure 5E:
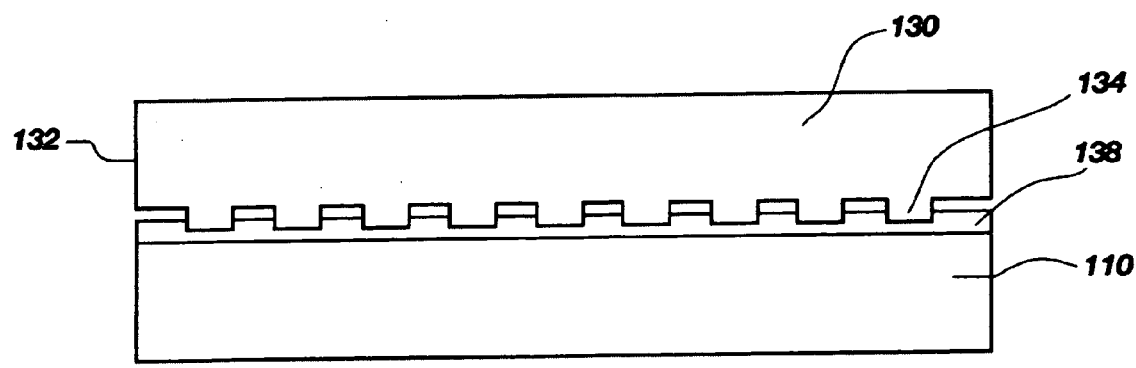
Figure 5F:
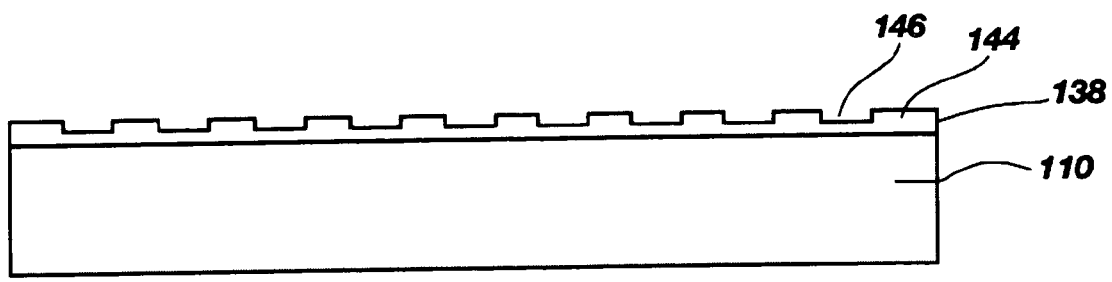

As shown in FIG. 5E, the mold 132 may be pressed against the SERS-active structure substrate 110 such that the protrusions 134 of the mold 132 are pressed into the layer 138 of deformable material. The protrusions 134 and recesses 136 of the mold 132 may form corresponding recesses 146 and protrusions 144 in the layer 138 of deformable material, as shown in FIG. 5F. The layer 138 of deformable material may be softened by heating the layer 138 to a temperature above the glass transition temperature of the material prior to pressing the mold 132 against the SERS-active structure substrate 110. The mold 132 may be removed subsequent to cooling the layer 138 of deformable material to a temperature below the glass transition temperature of the material. Alternatively, the mold 132 may be removed prior to cooling the layer 138 of deformable material if the layer 138 will maintain its shape (i.e., maintain the recesses 146 and protrusions 144) until the temperature of the layer 138 drops below the glass transition temperature of the material.

Figure 5G:
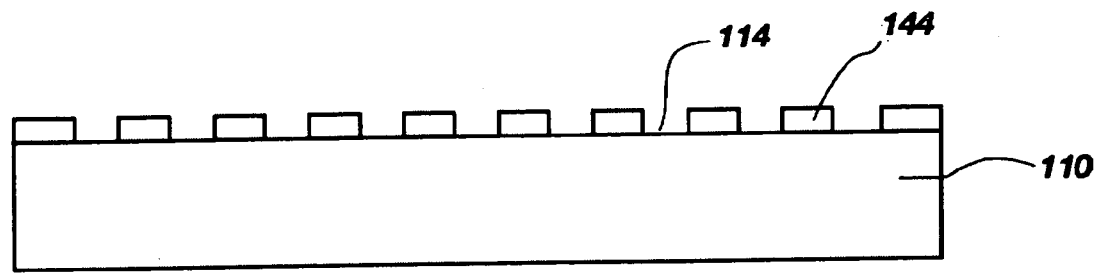

At least a portion of the patterned layer 138 of deformable material may be removed by, for example, reactive ion etching or chemical etching until regions of exposed silicon material 114 of the underlying SERS-active structure substrate 110 are exposed, as shown in FIG. 5G. As seen in FIG. 5G, only a portion of the protrusions 144 of the layer 138 of deformable material may remain, and the underlying SERS-active structure substrate 110 may be exposed at the regions where the recesses 146 were previously located.

The structure of FIG. 5G is substantially similar to the structure of FIG. 4C and includes exposed regions of silicon material 114 disposed at predetermined locations on the surface of the substrate 110. However, the structure of FIG. 5G includes protrusions 144 of a patterned layer of polymer material, while the structure of FIG. 4C includes a patterned oxide layer. These two structures are functionally equivalent, and the SERS-active structure 100 may be formed from the structure of FIG. 5G in the same manner as it is formed from the structure of FIG. 4C, as previously described herein.

Figure 6:
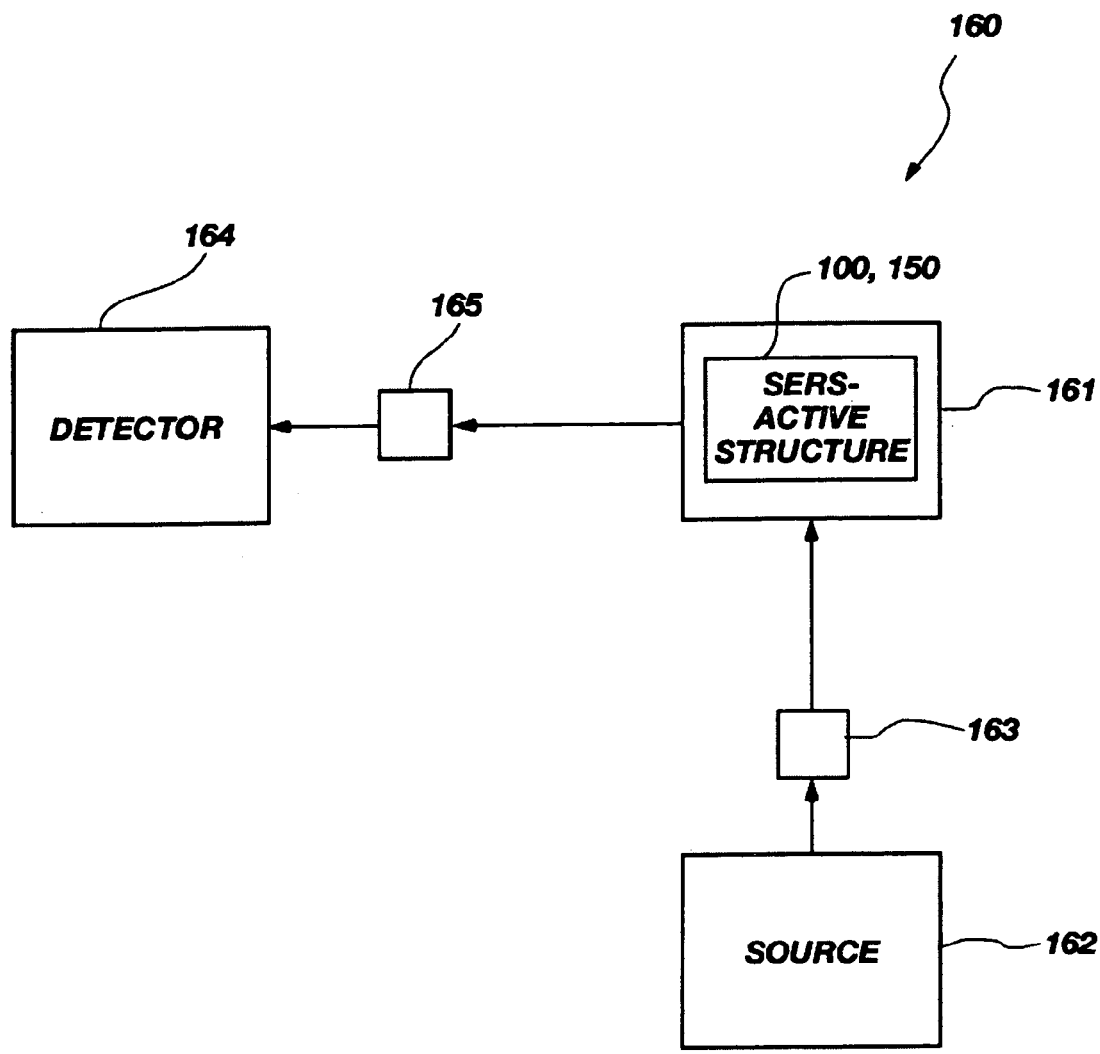
FIG. 6 is a schematic diagram of a system for performing surface enhanced Raman spectroscopy using the SERS-active structures of FIGS. 1–3.

An exemplary SERS system 160 according to the invention is illustrated schematically in FIG. 6. The system 160 may include one of the exemplary SERS-active structures 100 and 150, and may be used to perform surface enhanced Raman spectroscopy. The SERS system 160 may include a sample or analyte stage 161, an excitation radiation source 162, and a detector 164. The analyte stage 161 may include one of the SERS-active structure 100 and the SERS-active structure 150 (FIGS. 1–3). The SERS system 160 also may include various optical components 163 positioned between the excitation radiation source 162 and the analyte stage 161, and various optical components 165 positioned between the analyte stage 161 and the detector 164.

The excitation radiation source 162 may include any suitable source for emitting radiation at the desired wavelength, and may be capable of emitting a tunable wavelength of radiation. For example, commercially available semiconductor lasers, helium-neon lasers, carbon dioxide lasers, light emitting diodes, incandescent lamps, and many other known radiation emitting sources may be used as the excitation radiation source 162. The wavelengths that are emitted by the excitation radiation source 162 may be any suitable wavelength for properly analyzing the analyte using SERS. An exemplary range of wavelengths that may be emitted by the excitation radiation source 162 includes wavelengths between about 350 nm and about 1000 nm.

The excitation radiation emitted by the source 162 may be delivered either directly from the source 162 to the analyte stage 161 and the SERS-active structure 100, 150. Alternatively, collimation, filtration, and subsequent focusing of the excitation radiation may be performed by optical components 163 before the excitation radiation impinges on the analyte stage 161 and the SERS-active structure 100, 150.

The SERS-active structure 100, 150 of the analyte stage 161 may enhance the Raman signal of the analyte, as discussed previously herein. In other words, irradiation of the SERS-active structure 100, 150 by excitation radiation may increase the number photons inelastically scattered by an analyte molecule positioned near or adjacent to the SERS-active structure 100, 150.

The Raman scattered photons may be collimated, filtered, or focused with optical components 165. For example, a filter or a plurality of filters may be employed, either as part of the structure of the detector 164, or as a separate unit that is configured to filter the wavelength of the excitation radiation, thus allowing only the Raman scattered photons to be received by the detector 164.

The detector 164 receives and detects the Raman scattered photons and may include a monochromator (or any other suitable device for determining the wavelength of the Raman scattered photons) and a device such as, for example, a photomultiplier for determining the quantity of Raman scattered photons (intensity).

Ideally, the Raman scattered photons are scattered isotropically, being scattered in all directions relative to the analyte stage 161. Thus, the position of the detector 164 relative to the analyte stage 161 is not particularly important. However, the detector 164 may be positioned at, for example, an angle of 90° relative to the direction of the incident excitation radiation to minimize the intensity of the incident excitation radiation that may be incident on the detector 164.

To perform SERS using the system 160, a user may provide an analyte molecule or molecules adjacent to the SERS-active structure 100, 150. The analyte and the SERS-active structure 100, 150 are irradiated with excitation radiation or light from the source 162. Raman scattered photons scattered by the analyte are then detected by the detector 164.

The structures and systems disclosed herein may also be used to perform hyper-Raman spectroscopy. When excitation radiation impinges on an analyte molecule, a very small number of photons may be scattered at frequencies corresponding to the higher order harmonics of the excitation radiation, such as the second and third harmonic generations (i.e., twice or three times the frequency of the excitation radiation). Some of these photons may have a frequency that is Raman-shifted relative to the frequencies corresponding to the higher order harmonics of the excitation radiation. These higher order Raman-scattered photons can provide information about the analyte molecule that cannot be obtained by first order Raman spectroscopy. Hyper-Raman spectroscopy involves the collection and analysis of these higher order Raman-scattered photons.

The methods disclosed herein allow for the reproducible formation of SERS-active structures including nanoscale features having well controlled size, shape, location, and orientation. These structures allow for improved surface-enhanced Raman spectroscopy and may be used to produce molecular sensors having superior sensitivity relative to conventional SERS-active structures. The performance of nanoscale electronics, optoelectronics, molecular sensors, and other devices employing the Raman effect may be significantly improved by using the SERS-active structures disclosed herein. In addition, the methods disclosed herein allow for production of high quantities of SERS-active structures at relatively low cost.

Although the foregoing description contains many specifics, these are not to be construed as limiting the scope of the present invention, but merely as providing certain exemplary embodiments. Similarly, other embodiments of the invention may be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims are encompassed by the present invention.

What is claimed is:

1. A SERS system comprising:
    a SERS-active structure comprising:
        a substrate; and
        at least one nanowire disposed on the substrate, the at least one nanowire comprising:
            a core including a first material; and
            a coating including a SERS-active material;
    a light source configured to irradiate light onto the SERS-active structure; and
    a detector configured to receive Raman-scattered light scattered by an analyte located adjacent the SERS-active structure.

2. A method for performing SERS comprising:
    providing a SERS-active structure comprising:
        a substrate; and
        at least one nanowire disposed on the substrate, the at least one nanowire comprising:
            a core including a first material; and
            a coating including a SERS-active material;
    placing an analyte adjacent to the SERS-active structure;
    irradiating the analyte and the SERS-active structure with excitation radiation; and
    detecting Raman scattered radiation scattered by the analyte.

3. The method of claim 2, wherein the step of detecting comprises detecting Raman scatted radiation scattered by a single molecule.

4. A method for forming a SERS-active structure comprising:
    providing a substrate;
    forming a fractional monolayer of catalyst material on a surface of the substrate;
    annealing the fractional monolayer of catalyst material to promote self-assembly of at least one nanoisland of catalyst material;
    exposing the at least one nanoisland of catalyst material to a gas comprising a semiconductor material to promote the formation of at least one nanowire core of semiconductor material; and
    forming a coating of SERS-active material on the at least one nanowire core.

5. The method of claim 4, wherein the step of providing a substrate comprises providing a silicon substrate.

6. The method of claim 5, further comprising the steps of:
    providing a mold having an array of protrusions at predetermined locations on a surface of the mold, the protrusions having nanoscale dimensions;
    applying a layer of deformable material to a surface of the substrate;
    pressing the mold against the substrate, the array of protrusions in the surface of the mold forming an array of corresponding recesses in the layer of deformable material; and
    removing at least a portion of the layer of deformable material to expose at least a portion of the underlying substrate.

7. The method of claim 5, further comprising the steps of:
    oxidizing the surface of the silicon substrate to provide a thin oxide layer; and
    photolithographically forming at least one region of exposed silicon material in the thin oxide layer, the at least one region having a predetermined area and being located at a predetermined location on the surface of the substrate.

8. The method of claim 7, wherein the step of annealing the fractional monolayer of catalyst material comprises annealing the fractional monolayer of catalyst material to promote self-assembly of at least one nanoisland of catalyst material, the at least one nanoisland of catalyst material being located at the at least one region of exposed silicon material.

9. The method of claim 5, wherein the step of forming a fractional monolayer comprises forming a fractional monolayer of a material including titanium.

10. The method of claim 9, wherein the step of forming a fractional monolayer comprises chemical vapor deposition of a material including titanium by decomposition of $TiCl_4$.

11. The method of claim 10, wherein the step of exposing the at least one nanoisland of catalyst material to a gas comprising a semiconductor material comprises exposing the at least one nanoisland of catalyst material to a gas comprising one of $SiH_4$ and $SiH_2Cl_2$ to promote the formation of at least one silicon nanowire core.

12. The method of claim 4, wherein the step of forming a coating of SERS-active material on the at least one nanowire core comprises sputtering one of gold, silver, copper, platinum, palladium, and aluminum onto the at least one nanowire core.

13. The method of claim 4, wherein the step of forming a coating of SERS-active material on the at least one nanowire core comprises depositing one of gold, silver, copper, platinum, palladium, and aluminum onto the at least one nanowire core using one of thermal evaporation and electron beam evaporation.

14. The method of claim 4, wherein the step of forming a coating of SERS-active material on the at least one nanowire core comprises electroless plating the at least one nanowire core with one of gold, silver, copper, platinum, palladium, and aluminum.

15. The method of claim 4, wherein the step of exposing the at least one nanoisland of catalyst material to a gas comprising a semiconductor material to promote the formation of at least one nanowire core of semiconductor material comprises chemical vapor deposition of the semiconductor material.

* * * * *